United States Patent [19]

Styskin et al.

[11] 4,319,052
[45] Mar. 9, 1982

[54] METHOD FOR PREPARING STERICALLY HINDERED BIS- OR POLYPHENOLS

[76] Inventors: Evgeny L. Styskin, Khalturinskaya ulitsa 10, korpus 2, kv. 48; Yakov A. Gurvich, Sretensky bulvar, 6, kv. 61; Simona T. Kumok, Poklonnaya ulitsa, 4, kv. 32; Olga F. Starikova, Rublevskoe shosse, 89, korpus 2, kv. 52, all of Moscow; Grigory I. Rutman, Bashkirskaya ASSR, Revoljutsionnaya ulitsa, 7, kv. 6; Jury I. Michurov, Bashkirskaya ASSR, prospekt Lenina, 13, kv. 4, both of Sterlitamak; Vladimir A. Yanshevsky, ulitsa Kommunisticheskaya, 42, kv. 12, Novokuibyshevsk Kuibyshevskoi oblasti; Vladimir K. Gusev, ulitsa Utkina, 45a, kv. 55, Moscow; Alexandr G. Liakumovich, ulitsa Galeeva, 10, kv. 8, Kazan, all of U.S.S.R.

[21] Appl. No.: 822,374

[22] Filed: Aug. 5, 1977

[51] Int. Cl.³ .............................................. C07C 39/14
[52] U.S. Cl. ...................................... 568/727; 568/728
[58] Field of Search .................. 260/619 A; 568/805, 568/727

[56] References Cited

U.S. PATENT DOCUMENTS

| | | | |
|---|---|---|---|
| 2,290,603 | 7/1942 | Stevens et al. | 568/805 |
| 2,295,675 | 9/1942 | Meharg et al. | 568/805 |
| 2,327,938 | 8/1943 | Stevens et al. | 568/805 |
| 3,091,646 | 5/1963 | Leston | 568/805 |
| 3,296,316 | 1/1967 | Menworth | 568/805 |
| 3,408,408 | 10/1968 | Drew et al. | 260/619 A |
| 3,674,879 | 7/1972 | Trefenthal et al. | 260/619 A |
| 3,702,893 | 11/1972 | Fuchsman et al. | 260/619 A |
| 3,723,540 | 3/1973 | Michaels et al. | 260/619 A |
| 3,739,035 | 6/1973 | Webb et al. | 260/619 A |
| 3,761,525 | 9/1973 | Young et al. | 260/619 A |
| 3,836,590 | 9/1974 | Bundell et al. | 260/619 A |
| 4,020,113 | 4/1977 | Bundell et al. | 260/619 A |

Primary Examiner—Werren B. Lone
Attorney, Agent, or Firm—Haseltine and Lake

[57] ABSTRACT

A method for preparing sterically hindered bis- or polyphenols of the formula:

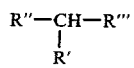

wherein R' is hydrogen, a $C_1$-$C_4$ alkyl; R" and R'" the same or different and are each:

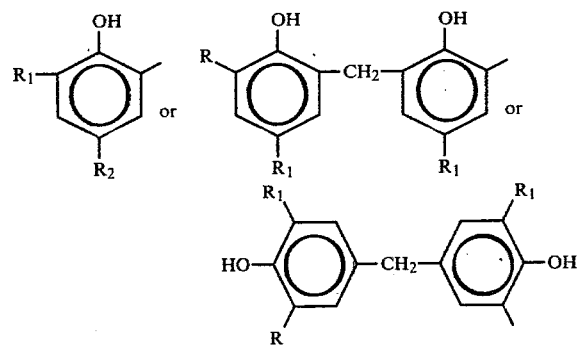

wherein R is a tertiary $C_4$-$C_8$ alkyl, $R_1$ and $R_2$ are the same or different and represent a $C_1$-$C_8$ alkyl or a $C_6$-$C_8$ cycloalkyl, or a $C_7$-$C_9$ aralkyl, which comprises reacting the starting sterically hindered 2,4,6-trialkylphenols of the formula:

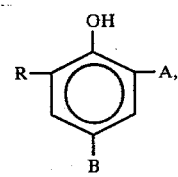

wherein A is a $C_1$-$C_8$ alkyl or a $C_6$-$C_8$ cycloalkyl or a $C_7$-$C_9$ aralkyl or a 3,5-dialkyl-2-hydroxybenzyl of the formula:

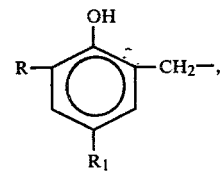

B is a $C_1$-$C_8$ alkyl, or a $C_6$-$C_8$ cycloalkyl, or a $C_7$-$C_9$ aralkyl, or a 3,5-dialkyl-4-hydroxybenzyl of the formula:

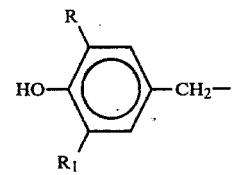

wherein $R_1$ and R are as identified above, with acetals, aldehydes or donors of $C_1$-$C_5$ aldehydes in an acidic medium at a temperature within the range of from 60° to 200° C. in the presence of an acidic catalyst, followed by isolation of the desired product.

The method according to the present invention makes it possible to prepare sterically hindered bis- or polyphenols in a single stage, whereby the process technology is substantially simplified as compared to those of the prior art. The method of the present invention precludes formation of waste water and atmospheric pollutants. The method ensures preparation of the desired products possessing high quality in high yield without any additional crystallization.

9 Claims, No Drawings

METHOD FOR PREPARING STERICALLY HINDERED BIS- OR POLYPHENOLS

FIELD OF THE INVENTION

The present invention relates to methods for preparing sterically hindered bis- or polyphenols which are useful as effective non-coloring, non-toxic and low-volatile stabilizing agents for rubbers, vulcanizates, plastics and other organic products.

Said stabilizing agents can be exemplified by such a well known compound as 2,2'-methylene-bis(4-methyl-6-tert. butylphenol) produced under commercial names as "Antioxidant 2246", KAO-5, and the like.

BACKGROUND OF THE INVENTION

Known in the art are various methods for preparing sterically hindered bisphenols of polyphenols. For example, currently used is a method for preparing 2,2'-methylene-bis-(4-methyl-6-tert.butylphenol), wherein the desired product is prepared by alkylation of 4-methylphenol with isobutylene in the presence of a catalyst, followed by separation and condensation of the resulting 2-tert.butyl-4-methylphenol with formaldehyde.

Condensation is conducted in the presence of acidic catalysts such as sulphuric acid. The process is carried out in an aqueous emulsion containing a surfactant and an organic solvent at a temperature within the range of from 75° to 90° C.

This prior art method has a disadvantage residing in the complicated technology of the process.

The process is performed in two stages, a great amount of waste water is formed (about 30 m³ per ton of the product) which is contaminated with surfactants and organic solvents. Besides, as the starting product in the process use is made of p-cresol which is a difficult material to obtain.

Due to p-cresol being a critical product, another method for the preparation of 2,2'-methylene-bis-(4-methyl-6-tert.butylphenol) from 2,6-ditert.butyl-4-methylphenol has been developed, based on the production of the latter rather readily from cheap and easily available phenol. The process is based on dealkylation of 2,6-ditert.butyl-4-methylphenol, followed by separation and condensation of the resulting 2-tert.butyl-4-methylphenol with formaldehyde.

One of the principal disadvantages of this method also resides in the formation of a great amount of acidic waste water containing surfactants and organic solvents. Purification of such waste water on a commercial scale is rather complicated and economically inefficient.

Also known in the art is a method for preparing 2,2'-methylene-bis(4-methyl-6-tert.butylphenol) which has certain advantages over the methods mentioned hereinabove, since it makes possible to eliminate the formation of waste water. According to this method, the desired product is obtained from 2,6-ditert.butyl-4-methylphenol in two stages, namely: dealkylation of 2,6-ditert.-butyl-4-methylphenol, followed by separation and condensation of the resulting 2-tert.butyl4-methylphenol with an acetal in the presence of an acidic catalyst at a temperature within the range of from 30° to 140° C.

This prior art process as well as those described hereinbefore are performed in two stages and require separation, in a pure form, of 2-tert.butyl-4-methylphenol having a strong unpleasant odor, high toxicity and volatility. Furthermore, a complicated process technology is required to perform all the above-discussed prior art methods.

Moreover, the prior art methods described hereinbefore make it possible to prepare only bisphenols. As regards polyphenols, known in the art are complicated multi-staged methods of preparing same. For example, polyphenols are prepared by reacting para-alkylphenols having with free ortho-positions with chloromethyl derivatives of 2,6-dialkylphenols according to the following scheme:

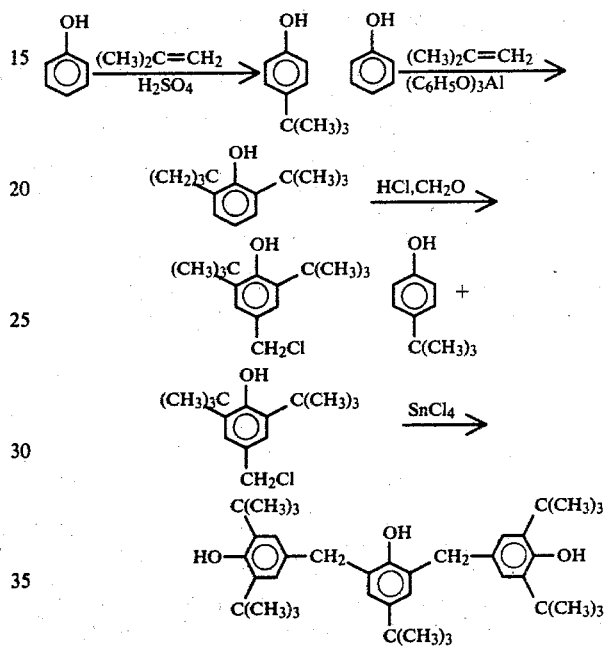

BRIEF SUMMARY OF THE INVENTION

It is a main object of the present invention to simplify the process technology.

It is another object of the present invention to increase the desired product yield and quality as to well as improve sanitary and hygienic working conditions for the personnel.

The main and other objects of the present invention are accomplished by the herein-proposed method for preparing sterically hingered bis- or polyphenols of the formula:

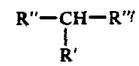

wherein R' is hydrogen or a $C_1$–$C_4$ alkyl, R" and R'" being either the same or different and each representing:

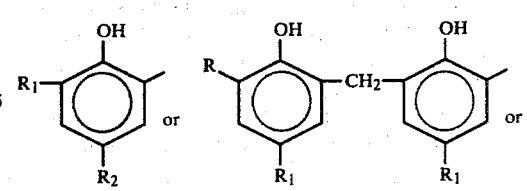

-continued

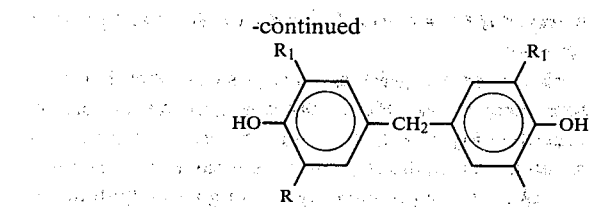

wherein R is a tertiary $C_4$-$C_8$ alkyl, $R_1$ and $R_2$ are the same or different and represent a $C_1$-$C_8$ alkyl or a $C_6$-$C_8$ cycloalkyl, or a $C_7$-$C_9$ aralkyl, in which method according to the present invention the starting sterically hindered 2,4,6-trialkylphenols of the formula:

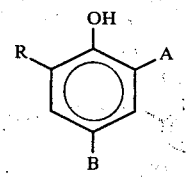

wherein A is a $C_1$-$C_8$ alkyl or a $C_6$-$C_8$ cycloalkyl, or a $C_7$-$C_9$ aralkyl or a 3,5-dialkyl-2-hydroxybenzyl of the formula:

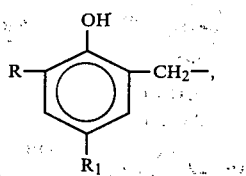

B is a $C_1$-$C_8$ alkyl, or a $C_6$-$C_8$ cycloalkyl, or a $C_7$-$C_9$ aralkyl, or a 3,5-sialkyl-4-hydroxybenzyl of the formula:

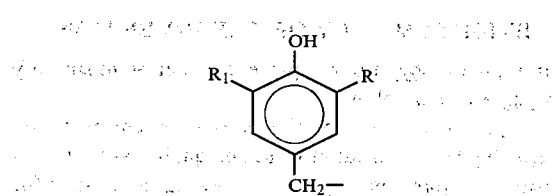

wherein R is a tertiary $C_4$-$C_8$ alkyl, $R_1$ is a $C_1$-$C_8$ alkyl, or a $C_6$-$C_8$ cycloalkyl, or a $C_7$-$C_9$ aralkyl, are reacted with acetals, aldehydes or donors of $C_1$-$C_5$ aldehydes in an acidic medium at a temperature within the range of from 60° to 200° C. in the presence of an acidic catalyst, followed by isolation of the desired product.

As the acidic catalysts it is preferable to use Brönsted acids such as sulfuric acid, ortho-phosphoric acid, polyphosphoric acid, perchloric acid, toluenesulphonic acid, napthalenesulphonic acid, cationites in H+ form and the like, or Lewis acids such as zinc chloride, aluminum chloride, ferric chloride, boron trifluoride and the like. These catalysts are readily separated from the desired product and ensure a high yield thereof, i.e. at least 78.7% of the reacted starting 2,4,6-trialkylphenols, predominantly at least 95% of the theoretical yield.

As the acetals, use is preferably made of commonly available and easily handled compounds of the formula:

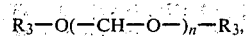

$$R_3-O(-CH-O-)_n-R_3,$$
$$|$$
$$R_4$$

wherein $R_3$ and $R_4$ are the same or different alkyls $C_1$-$C_5$; n=1 to 4.

Certain acetals comprise waste products from other syntheses; in particular, methylal is a waste product from the synthesis of isoprene rubber. Most preferable among acetals are methylal, ethylal, and dipentylformal; however, use may be made of other acetals such as dimethylacetal, diethylacetal, diisopropylacetal and the like.

As aldehydes it is preferred to use acetaldehyde, propionaldehyde, butyraldehyde, isobutyraldehyde, valeraldehyde and isovaleraldehyde because these comprise readily available and easy-to-handle reagents. It is also possible to use formaldehyde and other aldehydes.

As donors of $C_1$-$C_5$ aldehydes in an acidic medium, use can be made of cyclic polymers of aldehydes such as trioxane, paraldehyde, and 2,4,6-tri-isobutyl-1,3,5-trioxane, since these products are more stable upon storage and easier to handle as compared to monomeric aldehydes.

Among cyclic polymers, trioxane is most preferred, since the most valuable antioxidants are those sterically hindered bis- or polyphenols which have methylene bridges between aromatic rings.

As donors of $C_1$-$C_5$ aldehydes in an acidic medium use can be also made of linear polymers of aldehydes, since the latter polymers just as cyclic polymers of aldehydes, are more stable upon storage. Paraform is the most preferred linear polymeric aldehyde, since it, like trioxane, ensures incorporation of methylene bridges between aromatic rings thus providing for the formation of the most valuable methylenebisphenols or methylene-polyphenols.

DETAILED DISCLOSURE OF THE INVENTION

The method according to the present invention is performed in the following manner.

Into a four-necked reactor provided with a stirrer, thermometer, cooler, and a heating bath there are charged a sterically hindered 2,4,6-trialkylphenol such as 2,6-ditert. butyl-4-methylphenol, an acidic catalyst such as sulfuric acid or a cationite in H+-form, or zinc chloride and the mixture is heated to a predetermined temperature with stirring. While maintaining this temperature, while stirring for 0.5–2 hours, there is fed into the reactor an acetal such as methylal, or an aldehyde such as acetaldehyde, or a donor of a $C_1$-$C_5$ aldehyde in an acidic medium, such as paraform.

The process temperature is maintained within the range of from 60° to 200° C. On completion of the process, the catalyst is separated and the desired product is isolated by conventional techniques such as, for example, crystallization.

The yield of the desired products is as high as 78.7 to 99.1% of the theoretical, as calculated for the reacted sterically hindered 2,4,6-trialkylphenol, predominantly above 95%; for the most effective stabilizing agent, i.e., 2,2'-methylene-bis-(4-methyl-6-tert.butylphenol) the yield is as high as 97.8–99.1%. The method according to the present invention ensures the production of high-quality compounds. Thus, the melting point of 2,2'-methylene-bis(4-methyl-6-tert.butylphenol) prepared by the method of the present invention is 131°–131.5° C.

(according to the literature data, m.p. of the product is 131°–132° C.).

The method according to the present invention features certain advantages over the prior art methods. The selected reactants and conditions of interaction thereof ensure the production of the desired bisphenols or polyphenols from sterically hindered 2,4,6-trialkylphenols in a single stage, wherefore the process technology is substantially simplified and the sanitary and hygienic working conditions are improved, since no pure 4-methyl-2-tert.butylphenol possessing high toxicity, strong unpleasant odour and high volatility is evolved in the process. High-quality products are obtained in the process which require no additional crystallization. Bisphenols or polyphenols can be obtained from monophenols following the method according to the present invention, by appropriately selecting the reaction conditions. The unreacted starting products are recycled back into the process. The tertiary olefins resulting from the reaction are used in the preparation of the starting sterically hindered 2,4,6-trialkylphenols. The method according to the present invention completely eliminates the formation of waste water and atmospheric pollutants.

For a better understanding of the present invention, some specific examples illustrating the method for preparing sterically hindered bis- and polyphenols are given hereinbelow.

EXAMPLE 1

Into a reactor provided with a stirrer, thermometer and a heating bath there are charged 220 g (1 g.-mol) of 2,6-ditert.butyl-4-methylphenol, 2.2. g of concentrated sulfuric acid and the mixture is heated to the temperature of 120° C. While maintaining the temperature at 120° C., 94 g (1.24 g-mol) of methylal are fed into the reactor for 1.5 hour. On completion of the reaction, the catalyst is separated, volatile products are distilled under vacuum to give 143.0 g of 2,2'-methylene-bis(4-methyl-6-tert.butylphenol) which corresponds to 97.8% of theory as calculated for the reacted 2,6-ditert.butyl-4-methylphenol (conversion degree of the latter is 86.0%).

After a single recrystallization the resulting product has its melting point of 131°–131.5° C. (from the literature data m.p. is 131°–132° C.

The unreacted 2,6-ditert.butyl-4-methylphenol and methylal are recycled back into the process.

EXAMPLE 2

Into a reactor similar to that described in Example 1 hereinabove there are charged 220 g (1 g-mol) of 2,6-ditert.-butyl-4-methylphenol, 2.2 g of concentrated sulfuric acid and at the temperature of 120° C. 76 g (1.0 g-mol) of methylal are fed into the reactor for 1 hour. The reaction mass is treated following the procedure described in the foregoing Example 1 to give 112.9 g of 2,2'-methylene-bis-(4-methyl-6-tert.butylphenol) which constitutes 99.1% of theory, as calculated for the reacted 2,6-ditert.butyl-4-methylphenol (conversion of the latter is 67.0%). The unreacted methylal and 2,6-ditert.butyl-4-methylphenol are recycled back into the process.

EXAMPLE 3

Into the reactor described in the foregoing Example 1 there are charged 220 g (1.0 g-mol) of 2,6-ditert.butyl-4-methylphenol, 2.2 g of sulfuric acid and 44 g (1 g-mol) of acetaldehyde are fed into the reactor for one hour at the temperature of 125° C. On completion of the reaction, the reaction mass is treated following the procedure described in the foregoing Example 1 to give 124.6 g of 1,1,-bis-(5-methyl-3-tert.butyl-2-hydroxyphenyl)ethane which constitutes 96.4% of theory, as calculated for the reacted 2,6-ditert.butyl-4-methylphenol (conversion of the latter is 73%).

After a single recrystallization the resulting product has its melting point of 104°–104.5° C. (from the literature data m.p. of the product is 104.5° C.).

The unreacted 2,6-ditert.butyl-4-methylphenol and acetaldehyde are recycled back into the process.

EXAMPLE 4

Into the reactor described in Example 1 hereinbefore there are charged 212 g (0.5 g-mol) of 4,4'-methylene-bis-(2,6-ditert.butylphenol), 8.4 g of zinc chloride and 10 g (0.111 g-mol) of trioxane are added to the mixture over 30 minutes at the temperature of 200° C. On completion of the reaction, the catalyst is separated, the volatile products are distilled under vacuum to give 193.7 g of 2,2'-methylenebis-[4-(3,5-ditert.butyl-4-hydroxybenzyl)-6-tert.butylphenol] in the form of a resin having molecular weight of 736 (the theoretical molecular weight of the condensation product is 748).

EXAMPLE 5

Into the reactor described in the foregoing Example 1 there are charged 170 g (0.5 g-mol) of 2,2'-methylene-bis-(4-methyl-6-tert.butylphenol), 34 g of a cation-exchange resin in H+-form (sulfonated copolymer of styrene with divinylbenzene) and at the temperature of 160° C. 8.2 g (0.26 g-mol) of paraform (calculated for the 95% product) are added to the reaction mass over one hour. On completion of the reaction, the catalyst is separated, the volatile products are distilled under vacuum to give 141.9 g of a resin containing 46.1% by weight of the condensation product, i.e. 2,2'-methylene-bis-[4-methyl-6-(3-tert.butyl-5-methyl-2-hydroxybenzyl)phenol] and 53.9% by weight of the starting product. The thus-obtained resin can be used as an antioxidant.

EXAMPLE 6

Into the reactor described in Example 1 hereinbefore there are charged 282 g (1 g-mol) of 2,4,6-tritert.butylphenol, 9 g of a concentrated sulfuric acid and 110 g (1.17 g-mol) of dipentylformal are introduced into the reactor over 2 hours at the temperature of 60° C. On completion of the reaction, the catalyst is separated, volatile products are distilled under vacuum to give 120.7 g of the desired product, i.e. 2,2'-methylene-bis-(4,6-ditert.butylphenol) which constitutes 98.2% of theory, as calculated for the reacted 2,4,6-tritert.butylphenol (conversion of the latter is 53%).

After a single recrystallization the resulting product has its melting point of 141°–142° C.

The unreacted 2,4,6-tritert.butylphenol and dipentylformal are recycled back into the process.

EXAMPLE 7

Into the reactor described in Example 1 hereinbefore there are charged 155 g (0.5 g-mol) of 2,6-ditert.butyl-4-α-methylbenzenephenol, 3.2 g of para-toluenesulphonic acid and 21.9 g (0.255 g-mol) of isovaleraldehyde are added thereto at the temperature of 150° C. over 1.5 hour. On completion of the reaction, the catalyst is separated, the volatile products are distilled under vacuum to give 120.9 g of 1,1-bis-(6-tert.butyl-4-α-methylbenzylphenol)isopentane which corresponds to 95.8% of theory, as calculated for the reacted 2,6-ditert.butyl-4-α-methylbenzylphenol (conversion of the latter is 88%).

EXAMPLE 8

Into the reactor described in Example 1 hereinbefore there are charged 330 g (1.5 g-mol) of 2,6-ditert.butyl-4-methylphenol, 6.5 g of concentrated sulfuric acid and 152 g (2 g-mol) of methylal are added thereto over 2 hours at the temperature of 150° C. On completion of the reaction, the catalyst is separated, volatile products are distilled under vacuum to give 200.3 g of the desired product, i.e. 2,6-di-(5-methyl-3-tert.butyl-2-hydroxybenzyl)-para-cresol which constitutes 87.1% of the theory as calculated for the reacted 2,6-ditert.butyl-4-methylphenol (conversion of the latter is 100%).

After recrystallization the thus-prepared product has its melting point of 163°–163.5° C.

EXAMPLE 9

Into the reactor described in Example 1 there are charged 220 g (1.0 g-mol) of 2,6-ditert.butyl-4-methylphenol, 11 g of ortho-phosphoric acid and 66 g (1.5 g-mol) of acetaldehyde are added thereto at the temperature of 150° C. over one hour. On completion of the reaction, the catalyst is separated, volatile products are distilled under vacuum to give 210 g of a mixture of 1,1-bis-(5-methyl-3-tert.butyl-2-hydroxyphenol)ethane and 2,6-di-(5-methyl-3-tert.butyl-2-hydroxymethylbenzyl)-para-cresol. The resulting mixture can be used without any separation as an antioxidant. Conversion of 2,6-ditert.butyl-4-methylphenol is 99%.

EXAMPLE 10

Into the reactor described in Example 1 hereinbefore there are charged 123 g (0.5 g-mol) of 2-tert.butyl-6-cyclohexyl-4-methylphenol, 2.2 g of a concentrated sulfuric acid and the mixture is heated at the temperature of 120° C. Then at this temperature 47 g (1.12 g-mol) of methylal are added into the reactor over 1.5 hour. On completion of the reaction, the catalyst is separated, the volatile products are distilled under vacuum to give 163.1 g of 2,2'-methylenebis-(4-methyl-6-cyclohexylphenol) which constitutes 99.1% of theory, as calculated for the reacted 2-tert.butyl-6-cyclohexyl-4-methylphenol (conversion of the latter is 84%).

After recrystallization the resulting product has its melting point of 117°–117.5° C.

The unreacted 2-tert.butyl-6-cyclohexyl-4-methylphenol and methylal are recycled back into the process.

EXAMPLE 11

Into the reactor described in Example 1 hereinbefore there are charged 159 g (0.5 g-mol) of 2,6-ditert.butyl-4-tert.octylphenol, 2 g of concentrated sulfuric acid and 36 g (0.5 g-mol) of butyraldehyde are added into the reactor at the temperature of 125° C. over one hour. On completion of the reaction, the catalyst is separated, the volatile products are distilled under vacuum to give 103.3 g of the desired product, i.e. 1,1-bis-(3-tert.butyl-5-tert.octyl-2-hydroxyphenyl)butane whch corresponds to 95.3% of theory, as calculated for the reacted 2,6-ditert.butyl-4-tert.octylphenol (conversion of the latter is 75.0%).

The unreacted 2,6-ditert.butyl-4-tert.octylphenol and butyraldehyde are recycled back into the process.

EXAMPLE 12

Into the reactor described in Example 1 hereinbefore there are charged 234 g (1 g-mol) of 2-tert.octyl-4,6-xylenol, 2,4 g of a concentrated sulphur acid and 76 g (1 g-mol) of methylal are added thereto at the temperature of 100° C. over one hour. The reaction mass is treated following the procedure of the foregoing Example 11 to give 63.5 g of the desired product, i.e. 2,2'-methylene-bis-(4,6-dimethylphenol) which constitutes 81.1% of the theoretical yield as calculated for the reacted 2-tert.-octyl-4,6-xylenol (conversion of the latter is 61.2%).

The unreacted 2-tert.octyl-4,6-xylenol and methylal are recycled back into the process.

EXAMPLE 13

Into the reactor described in Example 1 hereinbefore there are charged 58.5 g (0.25 g-mol) of 2,6-ditert.butyl4-ethylphenol, 1 g of a concentrated sulfuric acid and 19 g (0.25 g-mol) of methylal are added into the reactor at the temperature of 130° C. over 30 minutes. The reaction mass is treated and 26.2 g of 2,2'-methylene-bis-(4-ethyl-6-tert.butylphenol) are thus obtained which corresponds to 98.9% of the theoretical yield calculated for the reacted 2,6-ditert.butyl-4-ethylphenol (conversion of the latter is 57.5).

After a single recrystallization a product is obtained which melts at 124.5°–125.0° C.

The unreacted 2,6-ditert.butyl-4-ethylphenol and methylal are recycled back into the process.

EXAMPLE 14

Into the reactor described in the foregoing Example 1 there are charged 141.0 g (0.5 g-mol) of 2-tert.butyl-4-methyl-6-cumylphenol, 1.5 g of a concentrated sulfuric acid and 52 g (0.5 g-mol) of ethylal are added to the mixture at the temperature of 130° C. for one hour. On completion of the reaction, the catalyst is separated, the unreacted 2-tert.-butyl-4-methyl-6-cumylphenol and ethylal are distilled under vacuum to give 62.5 g of the desired product, i.e. 2,2'-methylene-bis-(4-methyl-6-cumylphenol) which constitutes 78.7% of the theoretical yield calculated for the reacted 2-tert.butyl-4-methyl-6-cumylphenol (conversion of the latter is 68.5%). The unreacted products are recycled back to the process.

EXAMPLE 15

Into the reactor described in the foregoing Example 1 there are charged 70.5 g (0.25 g-mol) of 2-tert.hexyl-4-methyl-6-benzylphenol, 20 g of a cation-exchange resin in H+-form (sulfonated copolymer of styrene with divinylbenzene) and 17.4 g (0.3 g-mol) of propionaldehyde are added into the reactor at the temperature of 145° C. over 30 minutes. On completion of the reaction, the catalyst is separated, the volatile products are distilled under vacuum to give 31.4 g of 1,1-bis-(5-methyl-3-benzyl-2-hydroxyphenyl)propane which constitutes 91.1% of the theoretical yield calculated for the reacted 2-tert.hexyl-4-methyl-benzylphenol (conversion of the latter is 63.2%).

The unreacted 2-tert.hexyl-4-methyl-6-benzylphenol and propionaldehyde are recycled back to the process.

What is claimed is:

1. A method for preparing sterically hindered bis- or polyphenols of the formula:

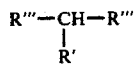

wherein R' is selected from the group consisting of hydrogen and a $C_1$-$C_4$ alkyl; R" and R'" are the same or different and are selected from the group consisting of:

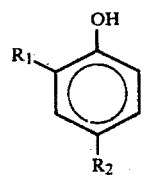 , 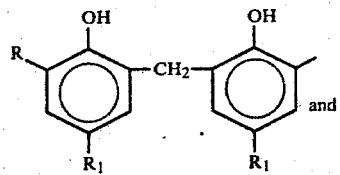 and

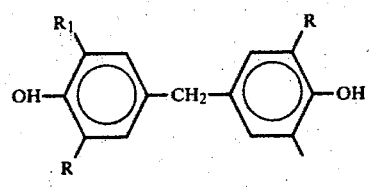

wherein R is a tertiary $C_4$-$C_8$ alkyl, $R_1$ and $R_2$ are the same or different and are selected from the group consisting of a $C_1$-$C_8$ alkyl, a $C_6$-$C_8$ cycloalkyl, a $C_7$-$C_9$ aralkyl, which comprises reacting a sterically hindered 2,4,6-trialkylphenol of the formula:

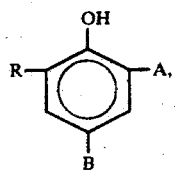

wherein A is selected from the group consisting of a $C_1$-$C_8$ alkyl, a $C_6$-$C_8$ cycloalkyl, a $C_7$-$C_9$ aralkyl and a 3,5-dialkyl-2-hydroxybenzyl of the formula:

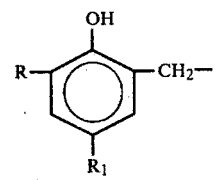

B is selected from the group consisting of a $C_1$-$C_8$ alkyl, a $C_6$-$C_8$ cycloalkyl, a $C_7$-$C_9$ aralkyl and a 3,5-dialkyl-4-hydroxybenzyl of the formula:

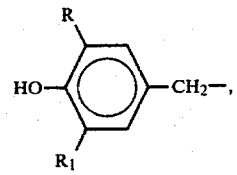

wherein R and $R_1$ are as identified above, with acetals, aldehydes or donors of $C_1$-$C_5$ aldehydes in an acidic medium at a temperature ranging from 60° to 200° C. in the presence of an acidic catalyst, followed by isolation of the desired product.

2. A method as claimed in claim 1, wherein the acidic catalysts are selected from the group consisting of Lewis acids and Brönsted acids.

3. A method as claimed in claim 1, wherein the acetal is a compound of the formula:

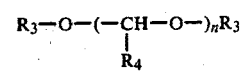

wherein $R_3$ and $R_4$ are the same or different and are $C_1$-$C_5$ alkyl, wherein n=1 to 4.

4. A method as claimed in claim 3, wherein the acetals are selected from the group consisting of methylal, ethylal and dipentylformal.

5. A method as claimed in claim 1, wherein the aldehydes are selected from the group consisting of acetaldehyde, propionaldehyde, butyraldehyde and isovaleraldehyde.

6. A method as claimed in claim 1, wherein the donors of $C_1$-$C_5$ aldehydes in an acidic medium are cyclic polymers of aldehydes.

7. A method claimed in claim 6, wherein as the cyclic polymer of the aldehyde is trioxane.

8. A method as claimed in claim 1, wherein the donors of $C_1$-$C_5$ aldehydes in an acidic medium are linear polymers of aldehydes.

9. A method as claimed in claim 8, wherein source of linear polymers of aldehydes is paraform.

* * * * *